(12) United States Patent
Govari et al.

(10) Patent No.: US 11,159,124 B2
(45) Date of Patent: Oct. 26, 2021

(54) SINE-WAVE GENERATION USING PULSED D-CLASS AMPLIFIER

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/812,563

(22) Filed: Mar. 9, 2020

(65) Prior Publication Data
US 2021/0281216 A1  Sep. 9, 2021

(51) Int. Cl.
*H03F 3/217*  (2006.01)
*A61B 18/00*  (2006.01)
(Continued)

(52) U.S. Cl.
CPC .............. *H03B 5/08* (2013.01); *H03F 3/217* (2013.01); *A61B 5/283* (2021.01); *A61B 18/1233* (2013.01); *A61B 18/1492* (2013.01); *A61B 2017/0019* (2013.01); *A61B 2017/00185* (2013.01); *A61B 2018/0072* (2013.01); *A61B 2018/0075* (2013.01); *A61B 2018/00351* (2013.01); *A61B 2018/00577* (2013.01); *A61B 2018/00702* (2013.01);
(Continued)

(58) Field of Classification Search
CPC .. A61B 2017/00185; A61B 2017/0019; A61B 2018/00702; A61B 2018/00708; A61B 2018/00726; A61B 2018/00732; A61B 2018/0072; A61B 2018/0075; A61B 2018/00767; A61B 2018/00827; A61B 2018/00869; A61B 2018/00892; G06F 1/022; H03B 5/00; H03B 5/08; H03B 28/00; H03B 2200/0064; H03F 3/217; H03F 3/2171
See application file for complete search history.

(56) References Cited

U.S. PATENT DOCUMENTS

| | | | |
|---|---|---|---|
| 4,415,962 A | 11/1983 | Kassakian | |
| 4,527,010 A | 7/1985 | Anazawa | |

(Continued)

FOREIGN PATENT DOCUMENTS

| | | | |
|---|---|---|---|
| CN | 108736847 A | 11/2018 | |
| EP | 398087 A2 | 11/1990 | |
| EP | 1233371 A2 | 8/2002 | |

OTHER PUBLICATIONS

Texas Instrument application note titled "AN-263 Sine Wave Generation Techniques," SNOA665C, Oct. 1999, Revised Apr. 2013.
(Continued)

*Primary Examiner* — Levi Gannon

(57) ABSTRACT

A sine wave generator includes a resonator circuit, a control circuit and a pulse generator. The resonator circuit is configured to receive energy pulses and to generate a resonator sinusoidal signal responsively to the energy pulses. The control circuit is configured to estimate a signal measure of the resonator sinusoidal signal, or of a signal derived from the resonator sinusoidal signal. The pulse generator is configured to generate the energy pulses responsive to the signal measure estimated by the control circuit, and to drive the resonator circuit with the energy pulses.

20 Claims, 3 Drawing Sheets

(51) Int. Cl.
*H03B 5/08* (2006.01)
*A61B 17/00* (2006.01)
*A61B 18/12* (2006.01)
*A61B 18/14* (2006.01)
*A61B 5/283* (2021.01)

(52) U.S. Cl.
CPC ............. *A61B 2018/00767* (2013.01); *A61B 2018/00827* (2013.01); *A61B 2018/00869* (2013.01); *A61B 2018/00892* (2013.01); *A61B 2018/1286* (2013.01)

(56) References Cited

U.S. PATENT DOCUMENTS

| | | | | |
|---|---|---|---|---|
| 4,654,573 | A * | 3/1987 | Rough | B60L 53/122 320/108 |
| 5,621,396 | A | 4/1997 | Flaxl | |
| 5,949,826 | A | 9/1999 | Iiyama | |
| 6,016,257 | A * | 1/2000 | Chang | H05B 41/2986 363/17 |
| 6,093,186 | A * | 7/2000 | Goble | A61B 18/1206 606/32 |
| 6,326,740 | B1 * | 12/2001 | Chang | H05B 41/3925 315/291 |
| 7,397,203 | B1 * | 7/2008 | Stevens | H05B 41/3921 315/307 |
| 7,667,548 | B2 | 2/2010 | Meier | |
| 8,981,860 | B2 | 3/2015 | Caffee | |
| 9,240,729 | B2 | 1/2016 | Kenny | |
| 9,554,871 | B2 | 1/2017 | Kovnatsky | |
| 9,590,565 | B2 | 3/2017 | Yuzurihara | |
| 9,641,164 | B2 | 5/2017 | Tohidian | |
| 9,667,208 | B2 | 5/2017 | Inukai | |
| 9,910,453 | B2 | 3/2018 | Wasserman | |
| 2003/0002279 | A1 * | 1/2003 | Fiene | E04B 9/32 362/147 |
| 2007/0086217 | A1 * | 4/2007 | Zhang | H05B 41/2827 363/17 |
| 2007/0108040 | A1 * | 5/2007 | Elkin | C01B 13/115 204/176 |
| 2009/0267669 | A1 * | 10/2009 | Kasai | H05B 6/686 327/164 |
| 2010/0301763 | A1 * | 12/2010 | Pan | H05B 41/2855 315/219 |
| 2011/0115562 | A1 * | 5/2011 | Gilbert | H03F 3/2171 330/262 |
| 2012/0043899 | A1 * | 2/2012 | Veskovic | H05B 41/295 315/200 R |
| 2012/0098351 | A1 * | 4/2012 | Ross | A61B 18/1233 307/104 |
| 2013/0345689 | A1 * | 12/2013 | Ruddenklau | A61B 18/12 606/33 |
| 2016/0058492 | A1 * | 3/2016 | Yates | A61B 18/1206 606/34 |
| 2018/0316310 | A1 | 11/2018 | Pentakota | |
| 2019/0286966 | A1 | 9/2019 | Zhang | |

OTHER PUBLICATIONS

Qi et al., "Design and Analysis of a Low Cost Wave Generator Based on Direct Digital Synthesis," Hindawi Journal of Electrical and Computer Engineering, vol. 2015, Article ID 367302, Nov. 2015.

European Search Report for corresponding EPA No. 21161318.7 dated Aug. 18, 2021.

* cited by examiner

SINE-WAVE GENERATION USING PULSED D-CLASS AMPLIFIER

FIELD OF THE INVENTION

The present invention relates generally to electronic circuits, and particularly to power-efficient sinewave oscillators.

BACKGROUND OF THE INVENTION

Sine wave generators, which are sometimes called sine wave inverters or sine wave oscillators, convert direct current (DC) from a power supply to an alternating current (AC) sine wave signal. Sine wave generators are common in the industry and used in numerous applications. In the area of cardiac intra-body medical procedures, sine wave generators may be used, for example, in procedures such as cardiac ablation, or the measurement of the impedance of electrodes that are inserted into the heart in a cardiac catheterization procedure.

Techniques to generate sinewaves are summarized, for example, in a Texas Instrument application note titled "AN-263 Sine Wave Generation Techniques," SNOA665C, October 1999, Revised April 2013.

U.S. Pat. No. 4,415,962 describes one technique to generate a sine wave, including two current sources that provide substantially constant currents. The current sources are employed to create complementary sinusoids which can be combined with greater ease to produce an ac output waveform.

In "Design and Analysis of a Low Cost Wave Generator Based on Direct Digital Synthesis," Hindawi Journal of Electrical and Computer Engineering, Volume 2015, Article ID 367302, November 2015, Qi et al describe a small sized and highly accurate economic signal generator based on direct digital synthesis (DDS) technology, which is capable of providing wave signals commonly used in experiments.

SUMMARY OF THE INVENTION

An embodiment of the present invention that is described herein provides a sine wave generator including a resonator circuit, a control circuit and a pulse generator. The resonator circuit is configured to receive energy pulses and to generate a resonator sinusoidal signal responsively to the energy pulses. The control circuit is configured to estimate a signal measure of the resonator sinusoidal signal, or of a signal derived from the resonator sinusoidal signal. The pulse generator is configured to generate the energy pulses responsive to the signal measure estimated by the control circuit, and to drive the resonator circuit with the energy pulses.

In an embodiment, the control circuit is configured to trigger the pulse generator to generate the energy pulses synchronously with a phase of the resonator sinusoidal signal, or of the signal derived from the resonator sinusoidal signal. In another embodiment, the control circuit is configured to estimate the signal measure by estimating a measure indicative of a voltage or current of the resonator sinusoidal signal, or of the signal derived from the resonator sinusoidal signal. In yet another embodiment, the control circuit is configured to estimate the signal measure by estimating a measure indicative of a phase of the resonator sinusoidal signal, or of the signal derived from the resonator sinusoidal signal.

In a disclosed embodiment, the resonator circuit is configured to output the resonator sinusoidal signal as an output of the sine wave generator. In an embodiment, the sine wave generator further includes a transformer configured to generate an output of the sine wave generator in response to the resonator sinusoidal signal. The sine wave generator may further include a series capacitor configured to prevent DC output.

In an example embodiment, the sine wave generator further includes current protection circuitry, configured to limit a current or a voltage of an output of the sine wave generator to a predefined current limit. In another embodiment, the control circuit is configured to set a pulse-width of the energy pulses generated by the pulse generator. In yet another embodiment, the control circuit is configured to set a pulse-amplitude of the energy pulses generated by the pulse generator.

There is additionally provided, in accordance with an embodiment of the present invention, a method for sine wave generation including, using a resonator circuit, receiving energy pulses and generating a resonator sinusoidal signal responsively to the energy pulses. A signal measure of the resonator sinusoidal signal, or of a signal derived from the resonator sinusoidal signal, is estimated. The energy pulses are generated responsive to the signal measure estimated by the control circuit, and the resonator circuit is driven with the energy pulses.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
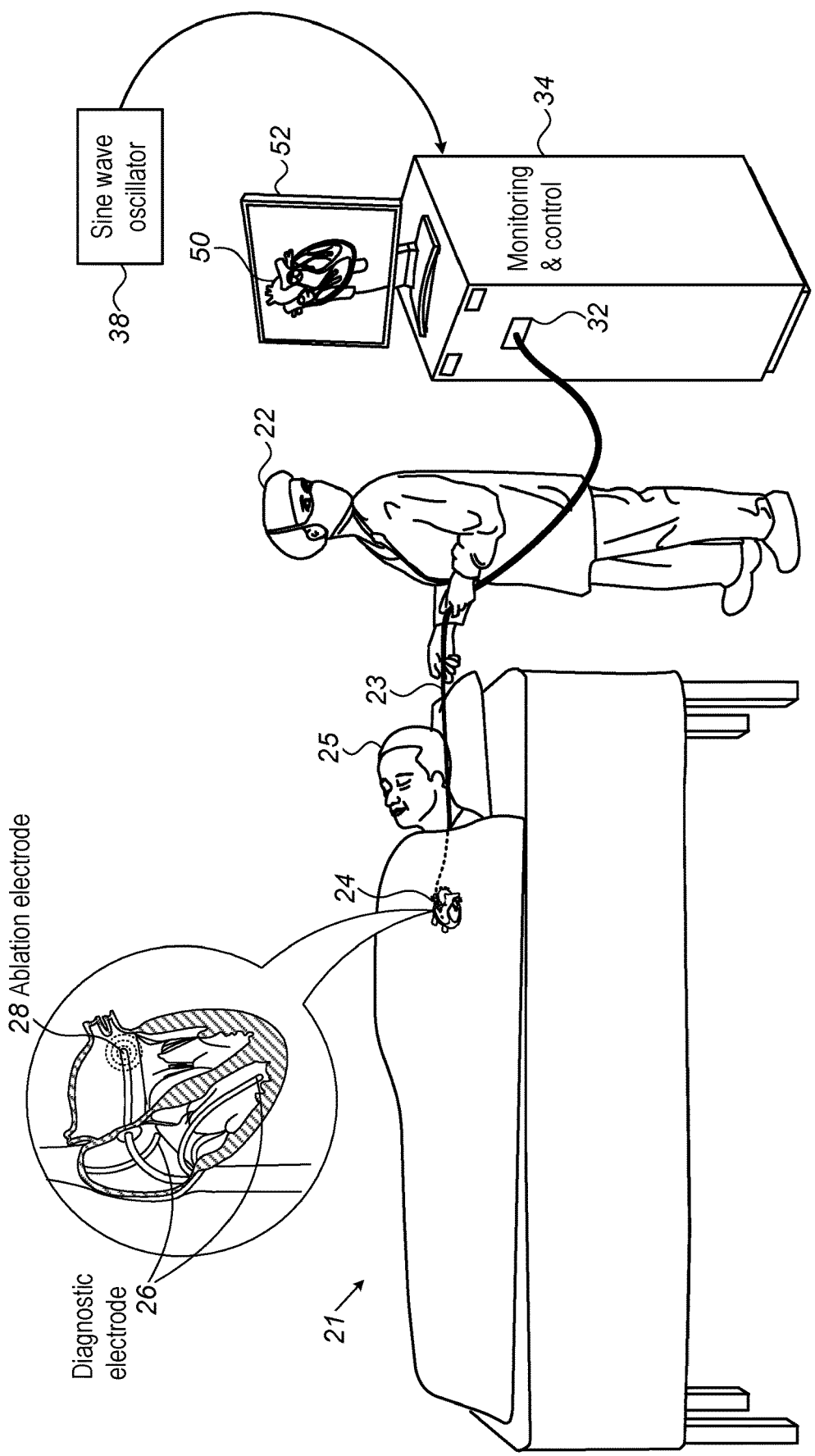
FIG. 1 is a schematic, pictorial illustration of an electro-anatomical system for the administration of intra-cardiac medical procedures, in accordance with an exemplary embodiment of the present invention.

Sine wave generators (which are sometimes called sine wave oscillators or sine wave inverters) are used in many applications, including medical, instrumentation, communication, radar, sonar and many others.

Conventional circuits to generate sine waves include, for example, a Wien Bridge Oscillator, a Phase-Shift Oscillator, a Colpitts Crystal Oscillator, and sine approximation (digital or otherwise) with filtering. These and other techniques are described in "AN-263 Sine Wave Generation Techniques," cited above.

Some of the approximation techniques comprise generating a square wave and then filtering the square wave to get a good sine wave approximation. In those cases, the square wave may be generated by a highly efficient D-class amplifier; however, a square wave comprises substantial energy in the odd harmonics ($\pi^2/8-1$, or approximately 23%); filtering the harmonics will, therefore, significantly reduce the efficiency of the oscillator.

Exemplary embodiments of the present invention that are disclosed herein provide improved methods and apparatus for high-efficiency sine wave generation. In some exemplary embodiments, a sine wave generator comprises a D-class amplifier that efficiently generates square pulses, and a resonator that is coupled to the D-class amplifier and oscillates at the desired frequency. The load of the sine wave generator may be connected directly to the resonator, or coupled to the resonator; e.g., through a transformer or a capacitor.

In some exemplary embodiments, the resonator oscillates at the characteristic resonator frequency (e.g., $1/(2*\pi*\sqrt{L*C})$). The sinusoidal signal produced by the resonator is referred to herein as "resonator sinusoidal signal." In some exemplary embodiments, the resonator sinusoidal signal has an envelope amplitude that decays over time, and the D-class amplifier stimulates the resonator with a square pulse when the amplitude of the resonator sinusoidal signal drops below a preset threshold. In some exemplary embodiments, the timing of the D-class pulses is synchronized to the phase of the resonator sinusoidal signal.

In some other exemplary embodiments, the sine wave generator is configured to adjust the voltage and/or the current that the sine wave generator delivers to the load by changing the pulse width that the D-class amplifier generates. In the exemplary embodiment that will be described hereinbelow, the sine wave generator comprises a control circuit that is configured to perform the control and adjustment functions described above.

In some other exemplary embodiments, the sine wave generator is configured to adjust the voltage and/or the current that the sine wave generator delivers to the load by changing the pulse amplitude that the D-class amplifier generates.

In some other exemplary embodiments, the sine wave generator is configured to adjust the voltage and/or the current that the sine wave generator delivers to the load by changing the pulse width and the pulse amplitude that the D-class amplifier generates.

More details will be described with reference to the exemplary embodiments hereinbelow.

System Description

FIG. 1 is a schematic, pictorial illustration of an electro-anatomical system 21 for the administration of intra-cardiac medical procedures, in accordance with an embodiment of the present invention. In some embodiments, system 21 is used for administrating a cardiac ablation procedure to a patient.

FIG. 1 depicts a physician 22 using an electro-anatomical catheter 23 to perform an ablation procedure in a heart 24 of a patient 25. Catheter 23 comprises, at its distal end, one or more diagnostics electrodes 26, and at least one ablation electrode 28. As would be appreciated, FIG. 1 depicts a catheter with three electrodes only for the sake of simplicity; other electrodes of the same or of different types may be used in alternative embodiments. The electrodes are coupled, through a connector 32, to a monitoring and control unit 34.

During the ablation procedure, the physician may position an ablation electrode 28 at or near the area of the heart which the physician wishes to ablate, using tracking and guidance techniques which are beyond the scope of the present disclosure. Once the ablation electrode is in place and all other preparatory procedures are completed, the physician may start the ablation by applying a high energy ablation signal through the ablation electrode to the ablation area in the heart. According to the exemplary embodiment described in FIG. 1, the ablation signal is a sine wave.

Monitoring and control unit 34 comprises a high-efficiency sine wave generator 38, which is configured to generate a sinewave by periodically exciting a resonator with energy pulses that are generated by a D-class amplifier. According to an exemplary embodiment, the voltage and current that the sine wave oscillator generates are automatically adjusted, and the power efficiency of the generator is high.

FIG. 1 mainly shows parts relevant to embodiments of the present invention; in particular, FIG. 1 focuses on sine wave generator 38 of monitoring and control unit 34. Other system elements, such as a processor, a signal-acquisition system, external ECG recording electrodes and their connections, filtering, digitizing, protecting circuitry, and others are omitted. However, for clarity and completeness, a monitor 52 is illustrated with an image 50 of the patient's 25 heart 24

Figure 2:
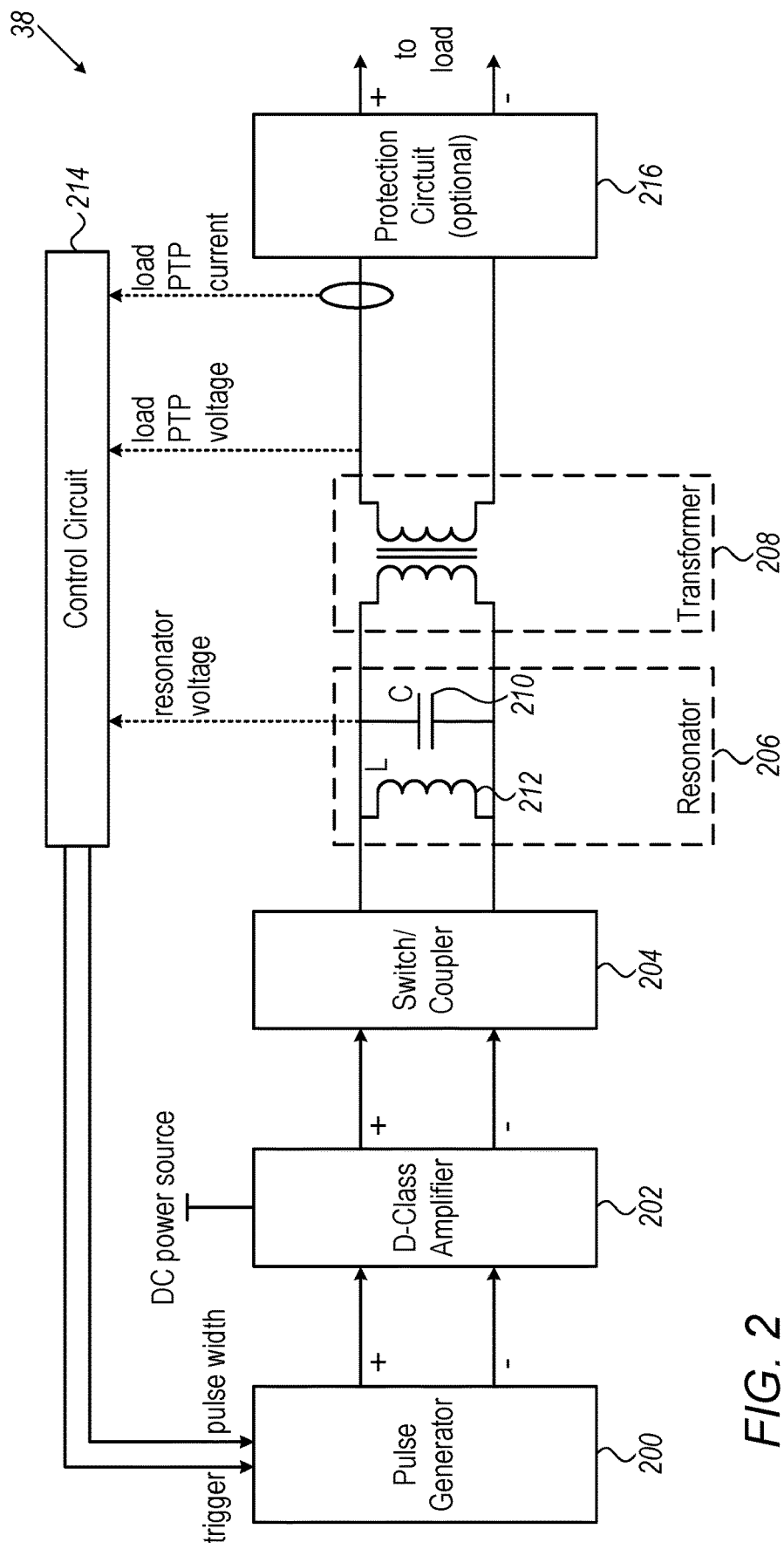
FIG. 2 is a circuit diagram that schematically illustrates a sine wave generator, in accordance with exemplary embodiments of the present invention.

FIG. 2 is a circuit diagram that schematically illustrates sine wave generator 38 (FIG. 1), in accordance with exemplary embodiments of the present invention. Sine wave generator 38 is configured to apply an output sinusoidal wave to a load, such as ablation electrode 28 (FIG. 1). The sine wave generator comprises a pulse generator 200, which is configured to generate energy pulses, typically in the form of square-wave voltage pulses; a D-class amplifier 202, which is configured to amplify the energy pulses; a switch/coupler 204; a resonator 206; a transformer 208, which is configured to transform the resonator sinusoidal signal to the output sinusoidal signal, while changing the AC voltage to the desired output voltage; and, a control circuit 214, which is configured to control the operation of pulse generator 200.

In some exemplary embodiments, pulse generator 200 receives a trigger indication from control circuit 214, and, responsively, generates pulses. In some exemplary embodiments, the pulse height may be up to 1 KV; in an embodiment, the pulse may be produced by a Field-Effect Transistor (FET). The width of the pulses is determined responsive to a pulse-width input that the pulse generator receives from the control circuit; in an exemplary embodiment the pulse width may vary between 0.1 and 1 microsecond, although any other suitable values can also be used.

D-Class amplifier 202 is coupled to a DC power source, and is configured to amplify the square wave output of pulse generator 200. The output of D-class amplifier 202 comprises energy pulses which are the power source of the sinusoidal wave that sine wave generator 38 delivers to the load.

Switch/coupler 204 is configured to couple the pulses that the D-class amplifier outputs to resonator 206. In some exemplary embodiments, switch/coupler 204 comprises a switch, operable to couple the D-class amplifier to the resonator only when pulses are present (so as not to short the resonator to 0 when no pulse is present); in other embodiments the switch/coupler comprises a diode. In an embodiment, the switch/coupler further comprises a capacitor, and the coupling is capacitive.

Resonator 206 comprises a capacitor 210 and an inductor 212. Once excited, the resonator oscillates at frequency $f=1/(2*\pi*\sqrt{L*C})$, where its impedance is maximal (theoretically infinite). The signal between the resonator output terminals is referred to as the resonator sinusoidal signal.

In some exemplary embodiments, control circuit 214 is configured to monitor the peak-to-peak (PTP) voltage and/or the peak-to-peak current that the sine wave generator applies to the load (referred to hereinbelow as a "signal measure" of the sinusoidal signal). When the voltage and/or current drops below a preset threshold, the control circuit sends a trigger pulse to pulse generator 200, initiating the generation of another pulse, which excites resonator 206 with additional energy.

According to exemplary embodiments, the pulses that are coupled to the resonator must be synchronized to the phase of the voltage in the resonator. To that end, control circuit 214 further monitors a phase measure of the resonator, and times the trigger output so that the new pulse will be synchronized with the oscillation in the resonator.

In some exemplary embodiments, control circuit 214 is further configured to control the width of the pulses that pulse generator 200 generates. Wider pulses typically transfer more energy, at the cost of sine wave distortions.

Lastly, sine wave generator 38 may optionally comprise a protection circuitry 216, which is configured to limit the current through the load to a predefined current limit, and/or limit the voltage of the output signal applied to the load to a predetermined voltage limit.

In summary, according to the exemplary embodiment illustrated in FIG. 2, a resonator, which is excited by a square pulse, generates a sine wave and drives the load through a transformer; when the oscillation decays below a threshold, the control circuit triggers a new pulse at the appropriate phase. The square pulse is amplified by a high efficiency D-class amplifier, and, as a result, the overall efficiency of the sine wave generator may be high.

In an exemplary embodiment, the frequency of the sine wave is 0.5 MHz, and the voltage of the pulses that the D-class amplifier send to the resonator is up to 200V (corresponding to a maximum ablation power of 90 W, assuming a 250 Ohm load). These numerical values are chosen purely by way of example. In alternative exemplary embodiments, any other suitable numerical values can be used.

As would be appreciated, the exemplary circuit diagram illustrated in FIG. 2 is depicted purely for the sake of conceptual clarity. In alternative exemplary embodiments of the present invention, for example, negative rather than positive signals may be used in some or in all the circuit elements. In other exemplary embodiments, some or all elements 200, 202, 204 206 and 208 may have unipolar rather than bipolar inputs and/or outputs (referenced to a common ground). In some exemplary embodiments, there is no transformer, and the resonator output is directly coupled to the load; in an embodiment the resonator is coupled to the load through a capacitor and in another exemplary embodiment, the transformer is coupled to the load through a capacitor, to prevent DC current.

In some exemplary embodiments, resonator 202 may be replaced by more complex resonators, having a plurality of stages, as is known in the art.

In some exemplary embodiments, switch/coupler 204 is omitted; instead, the D-class amplifier is configured as "open-drain" (e.g., the D-class amplifier drives the output only when the input pulse is high).

In some exemplary embodiments, Root-Mean-Square (RMS) rather than PTP sensing of the voltage and/or the current are used; in other embodiments, the PTP measurement is low-pass filtered. In yet another exemplary embodiment, no sensing of the voltage or current are done, and the timing of the pulses that pulse generator 200 generates is fixed (for example, in a fixed-load application).

Some of the circuit elements described with reference to FIG. 2 may be merged with one another, and/or sub-divided in a different way; for example, the pulse generator may be merged with the D-class amplifier and/or the control circuit.

Figure 3:
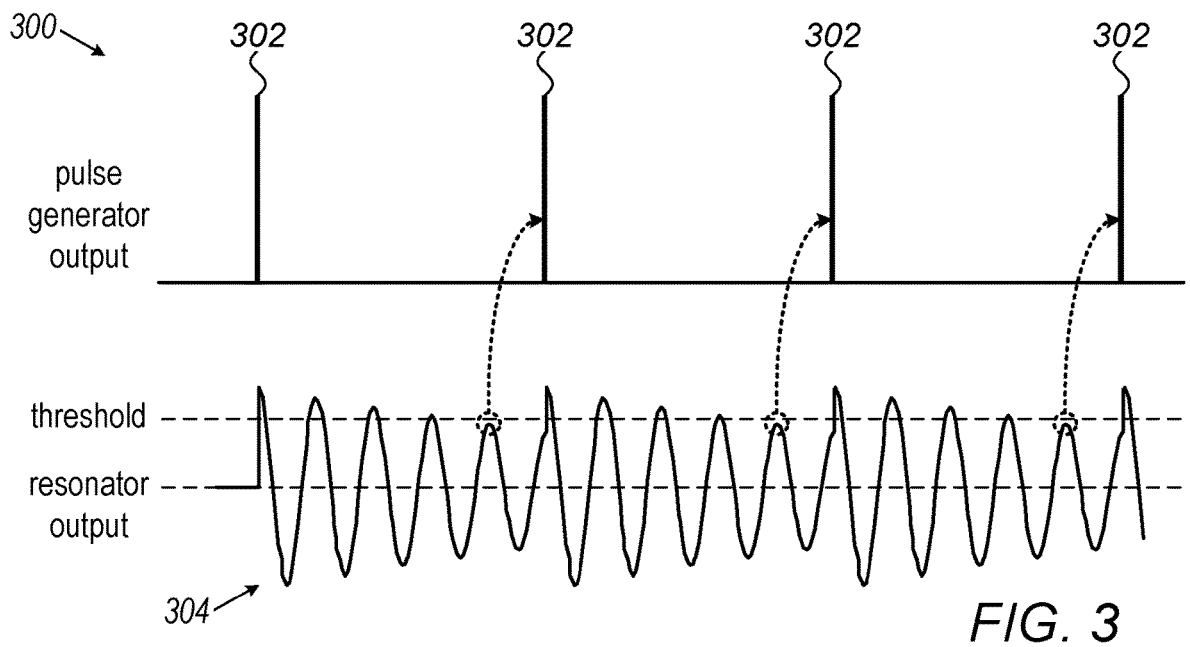
FIG. 3 is a graph that schematically illustrates the voltages of a pulse generator and a resonator against a horizontal time axis, in accordance with exemplary embodiments of the present invention.

FIG. 3 is a graph 300 that schematically illustrates the voltages of pulse generator 200 and resonator 206 (FIG. 2) against a horizontal time axis, in accordance with exemplary embodiments of the present invention. The pulse generator applies pulses 302, which are in phase with a sine wave 304 in the resonator circuit. Except for the first pulse 302, which starts when the resonator is not oscillating, all pulses 302 are generated when the sine wave is at a local maximum.

As indicated by the dashed arrows, the control circuit generates new pulses 302 when the oscillation peak voltage drops below the marked threshold; the new pulse restores the oscillation amplitude.

As would be appreciated, the decay rate and the relative threshold position are shown merely as an example; in embodiments, other rates and relative thresholds may be used.

Figure 4:
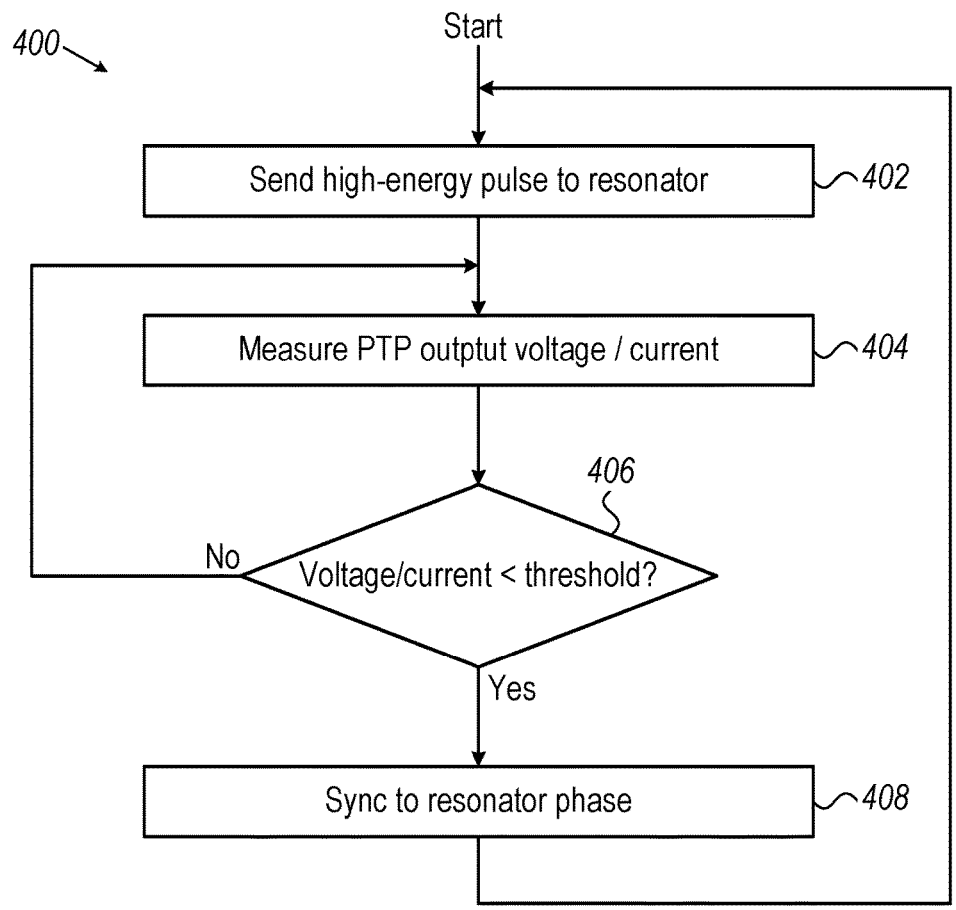
FIG. 4 is a flowchart that schematically illustrates a method for the generation of a sine wave, in accordance with exemplary embodiments of the present invention.

FIG. 4 is a flowchart 400 that schematically illustrates a method for the generation of a sine wave, in accordance with exemplary embodiments of the present invention. The flowchart is executed by the relevant components of the sine wave generator, illustrated in FIG. 2, including pulse generator 200, D-class amplifier 202, switch/coupler 204, resonator 206 and control circuit 214.

The flowchart starts at a sending high energy pulse step 402, wherein the pulse generator generates a pulse, the D-class amplifier amplifies the pulse and the switch-coupler sends the amplified pulse to the resonator, which starts oscillating, sending a sine wave to the load.

Next, in a Measuring PTP step 404, the control circuit measures the voltage and/or the current of the sine wave that is sent to the load. In a Comparing Voltage/Current step 406 the control circuit compares the measure of the voltage or the current to a preset threshold. The control circuit will remain in a loop comprising steps 404 and 406 as long as the voltage or current is not below the preset threshold. When the voltage/current drops below the threshold, the control circuit will enter a Synching to Phase step 408, wait for a suitable phase of the sine wave (e.g. 90°), and then re-enter step 402, to generate another pulse and inject more energy to the resonator.

As would be appreciated, the example flowchart illustrated in FIG. 4 is depicted purely for the sake of conceptual clarity. Other suitable flowcharts may be used in alternative embodiments. For example, flowchart 400 may comprise steps to evaluate distortions in the output sinusoidal signal and modify the pulse-width that the control unit applies to the pulse generator accordingly. In embodiments, some or all the steps of flowchart 400 may be executed concurrently.

In various exemplary embodiments, the different elements of sine wave generator 38 may be implemented using suitable hardware, such as one or more Application-Specific Integrated Circuit (ASIC), one or more Field-Programmable Gate Array (FPGA), discrete components or a combination thereof.

Although the exemplary embodiments described herein mainly address intra-cardiac applications such as cardiac ablation, the disclosed techniques can also be used for generating sinewaves for measurement of the impedance of intra-cardiac catheter electrodes, and/or for measurement of contact with tissue or proximity to tissue. Moreover, the methods and systems described herein can also be used in other applications, including other suitable areas where sine wave signals are used.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A sine wave generator, comprising:
a resonator circuit, configured to receive energy pulses and to generate a resonator sinusoidal signal responsively to the energy pulses;
a control circuit, configured to estimate a signal measure of the resonator sinusoidal signal, or of a signal derived from the resonator sinusoidal signal;
a pulse generator, configured to generate the energy pulses responsive to the signal measure estimated by the control circuit, and to drive the resonator circuit with the energy pulses; and
an amplifier configured to amplify the energy pulses from the pulse generator, wherein the control circuit is configured to trigger a new pulse from the pulse generator when the sinusoidal signal falls below a predetermined threshold and a suitable phase is achieved and stimulate the resonator circuit, the control circuit is configured to monitor a phase measure of the resonator circuit and times the trigger output so that the new pulse will be synchronized with an oscillation in the resonator circuit.

2. The sine wave generator according to claim 1, wherein the control circuit is configured to trigger the pulse generator to generate the energy pulses synchronously with a phase of the resonator sinusoidal signal, or of the signal derived from the resonator sinusoidal signal.

3. The sine wave generator according to claim 1, wherein the control circuit is configured to estimate the signal measure by estimating a measure indicative of a voltage or current of the resonator sinusoidal signal, or of the signal derived from the resonator sinusoidal signal.

4. The sine wave generator according to claim 1, wherein the control circuit is configured to estimate the signal measure by estimating a measure indicative of a phase of the resonator sinusoidal signal, or of the signal derived from the resonator sinusoidal signal.

5. The sine wave generator according to claim 1, wherein the resonator circuit is configured to output the resonator sinusoidal signal as an output of the sine wave generator.

6. The sine wave generator according to claim 1, further comprising a transformer, configured to generate an output of the sine wave generator in response to the resonator sinusoidal signal.

7. The sine wave generator according to claim 6, further comprising a series capacitor configured to prevent DC output.

8. The sine wave generator according to claim 1, further comprising a current protection circuitry, configured to limit a current or a voltage of an output of the sine wave generator to a predefined current limit.

9. The sine wave generator according to claim 1, wherein the control circuit is configured to set a pulse-width of the energy pulses generated by the pulse generator.

10. The sine wave generator according to claim 1, wherein the control circuit is configured to set a pulse-amplitude of the energy pulses generated by the pulse generator.

11. A method for sine wave generation, comprising:
using a resonator circuit, receiving energy pulses and generating a resonator sinusoidal signal responsively to the energy pulses;
using a control circuit, estimating a signal measure of the resonator sinusoidal signal, or of a signal derived from the resonator sinusoidal signal;
generating the energy pulses responsive to the signal measure estimated by the control circuit, and driving the resonator circuit with the energy pulses; and
using an amplifier configured to amplify the energy pulses from the pulse generator, wherein the control circuit is configured to trigger a new pulse from the pulse generator when the sinusoidal signal falls below a predetermined threshold and a suitable phase is achieved and stimulate the resonator circuit to improve efficiency, the control circuit is configured to monitor a phase measure of the resonator circuit and times the trigger output so that the new pulse will be synchronized with an oscillation in the resonator circuit.

12. The method according to claim 11, further comprising triggering the pulse generator to generate the energy pulses synchronously with a phase of the resonator sinusoidal signal, or of the signal derived from the resonator sinusoidal signal.

13. The method according to claim 11, wherein estimating the signal measure comprises estimating a measure indicative of a voltage or current of the resonator sinusoidal signal, or of the signal derived from the resonator sinusoidal signal.

14. The method according to claim 11, wherein estimating the signal measure comprises estimating a measure indicative of a phase of the resonator sinusoidal signal, or of the signal derived from the resonator sinusoidal signal.

15. The method according to claim 11, further comprising outputting the resonator sinusoidal signal as an output of the sine wave generator.

16. The method according to claim 11, further comprising generating an output of the sine wave generator by a transformer in response to the resonator sinusoidal signal.

17. The method according to claim 16, further comprising preventing DC output by a series capacitor.

18. The method according to claim 11, further comprising limiting a current or a voltage of an output of the sine wave generator to a predefined current limit.

19. The method according to claim 11, wherein generating the energy pulses comprises setting a pulse-width of the energy pulses.

20. The method according to claim 11, wherein generating the energy pulses comprises setting a pulse-amplitude of the energy pulses.

* * * * *